United States Patent
Siegel et al.

(10) Patent No.: US 7,687,773 B2
(45) Date of Patent: *Mar. 30, 2010

(54) SUB-MILLIMETER WAVE FREQUENCY HETERODYNE DETECTOR SYSTEM

(75) Inventors: Peter H. Siegel, La Canada, CA (US); Robert Dengler, Walnut, CA (US); Eric R. Mueller, West Suffield, CT (US)

(73) Assignees: California Institute of Technology, Pasadena, CA (US); Coherent, Inc., Santa Clara, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/214,760

(22) Filed: Jun. 20, 2008

(65) Prior Publication Data

US 2009/0065697 A1    Mar. 12, 2009

Related U.S. Application Data

(63) Continuation of application No. 10/956,734, filed on Oct. 1, 2004, now Pat. No. 7,507,963.

(60) Provisional application No. 60/507,980, filed on Oct. 1, 2003.

(51) Int. Cl.
  *G01J 5/02* (2006.01)
(52) U.S. Cl. .................................. 250/330
(58) Field of Classification Search .................. 250/330
  See application file for complete search history.

(56) References Cited

U.S. PATENT DOCUMENTS

| | | | |
|---|---|---|---|
| 4,461,039 A | 7/1984 | Hersman | 455/326 |
| 6,388,799 B1 | 5/2002 | Arnone et al. | 359/326 |
| 7,507,963 B2 * | 3/2009 | Siegel et al. | 250/330 |
| 2007/0257194 A1 | 11/2007 | Mueller | 250/341.8 |

FOREIGN PATENT DOCUMENTS

GB    2 359 716 A    8/2001

OTHER PUBLICATIONS

M.F. Kimmitt, entitled "Restrahlen to T-Rays—100 Years of Terahertz Radiation," *Journal of Biological Physics* (Kluwer Academic Publishers, The Netherlands), vol. 29, No. 2, Jun. 2003, pp. 77-85.

(Continued)

*Primary Examiner*—David P Porta
*Assistant Examiner*—Shun Lee
(74) *Attorney, Agent, or Firm*—Morrison & Foerster LLP

(57) ABSTRACT

The present invention relates to sub-millimeter wave frequency heterodyne imaging systems. More specifically, the present invention relates to a sub-millimeter wave frequency heterodyne detector system for imaging the magnitude and phase of transmitted power through or reflected power off of mechanically scanned samples at sub-millimeter wave frequencies.

37 Claims, 6 Drawing Sheets

OTHER PUBLICATIONS

Poster by P.H. Siegel et al. (with description sheet appended), entitled "Scanned-Pixel Terahertz Heterodyne Imaging," exhibited at *Terahertz GAP, Meeting of the British Royal Society*, London, Jun. 5, 2003, 2 pages in length (also included is an additional color printout of the poster for review).

M. Coulombe et al., "Submillimeter-Wave Polarimetric Compact Ranges for Scale-Model Radar Measurements," *IEEE MTT-S International* (2002), vol. 3, pp. 1583-1586.

G.B DeMartinis et al., "A 1.56 THz spot Scanning Radar Range for Fully Polarimetric W-Band Scale Model Measurements," *Antenna Measurements Techniques Association* (Oct. 2000), 6 pages in length.

J.C. Dickinson et al., "High Resolution Imaging using 325 GHz and 1.5 THz Transceivers," *Fifteenth International Symposium on Space Terahertz Technology*, Apr. 27-29, 2004, 8 pages in length.

T.M. Goyette et al., "A 1.56 THz compact radar range for W-band imagery of scale-model tactical targets," *Proc. SPIE*, vol. 4053, Aug. 2000, pp. 615-622.

E.R. Mueller et al., "Power and Spatial Mode Measurements of Sideband generated, Spatially Filtered, Submillimeter Radiation," *IEEE Transactions on Microwave Theory and Techniques*, vol. 42, No. 10, Oct. 1994, pp. 1891-1895.

J.C.S. Moraes et al., "The $^{13}CH_3OH$ Optically Pumped Far-Infrared Laser: New Lines and Frequency Measurements," *IEEE Journal of Quantum Electronics*, vol. 32, No. 10, Oct. 1996, pp. 1737-1739.

X.-C. Zhang, "Three-dimensional terahertz wave imaging," *Phil. Trans. R. Soc.Lond. A*, vol. 362 , Feb. 2004, pp. 283-299.

S. Wang et al., "Pulsed terahertz tomography," *Journal of Physics D: Applied Physics*, vol. 37, Feb. 2004, pp. R1-R36.

E.R. Mueller, "Frequency-Shifting Submillimeter Single-Sideband Receiver," *International Journal of Infrared and Millimeter Waves*, vol. 15, No. 4, Apr. 1994, pp. 665-670.

P.H. Siegel, "Terahertz Technology," *IEEE Transactions on Microwave Theory and Techniques*, vol. 50, No. 3, Mar. 2002, pp. 910-928.

X.-C. Zhang, "Terahertz wave imaging: horizons and hurdles," *Physics in Medicine and Biology*, vol. 47, Nov. 2002, pp. 3667-3677.

S.P. Mickan et al., "T-Ray Sensing and Imaging," *International Journal of High Speed Electronics and Systems*, vol. 13, No. 2, Jul. 2003, pp. 251-326.

D. Mittleman, "Terahertz Imaging," in *Sensing with Terahertz Radiation*, editor: D. Mittleman, Springer Series in Optical Sciences, Springer-Verlag, Berlin, May 2002, pp. 117-153.

P.H. Siegel et al., "2.5-THz GaAs Monolithic Membrane-Diode Mixer," *IEEE Transactions on Microwave Theory and Techniques*, vol. 47, No. 5, May 1999, pp. 596-604.

J.L. Doane, "Broadband superheterodyne tracking circuits for millimeter-wave measurements," *Rev. Sci. Instrum.*, vol. 51, No. 3, Mar. 1980, pp. 317-320.

W.R. McGrath et al., "Hot-electron superconductive mixers for THz frequencies," *SPIE Conference of Terahertz Spectroscopy and Applications*—San Jose, California, vol. 3617, Jan. 1999, pp. 80-88.

A. Barkan et al., "Measurement of the linewidth of a terahertz quantum cascade laser," *CLEO/QELS Conference*, Baltimore, Maryland, Jun. 1-6, 2003, 3 pages in length.

I. Mehdi et al., "THz Local Oscillator Sources: Performance and Capabilities," *Proceedings of SPIE Conference*—Walkola, Hawaii, vol. 4855, Aug. 22-28, 2002, pp. 435-446.

E.R. Brown et al., "Photomixing up to 3.8 THz in low-temperature-grown GaAs," *Appl. Phys. Lett.*, vol. 66, No. 3, Jan. 16, 1995, pp. 285-287.

P.H. Siegel et al., "Measurements on a 215-GHz Subharmonically Pumped Waveguide Mixer Using Planar Back-to-Back Air-Bridge Schottky Diodes," *IEEE Transactions on Microwave Theory and Techniques*, vol. 41, No. 11, Nov. 1991, pp. 1913-1921.

I. Mehdi et al., "An All Solid-State 640 GHz Subharmonic Mixer," *IEEE MTT-S Int. Microwave Symp. Dig.*, Jun. 1998, pp. 403-405.

I. Mehdi et al., "600 GHz Planar-Schottky-Diode Subharmonic Waveguide Mixers," *IEEE MTT-S Int. Microwave Symp. Dig.*, Jun. 1996, pp. 377-380.

H. Eisele et al., "High-Performance InP Gunn Devices for Fundamental-Mode Operation in D-Band (110-170 GHz)," *IEEE Microwave and Guided Wave Letters*, vol. 5, No. 11, Nov. 1995, pp. 385-387.

H. Wang et al., "Power-Amplifier Modules Covering 70-113 GHz Using MMICs," *IEEE Transactions on Microwave Theory and Techniques*, vol. 49, No. 1, Jan. 2001, pp. 9-16.

E.R. Mueller et al., "2.5 THz Laser Local Oscillator for the EOS Chem 1 Satellite," *Proc. 9th Int. Conf. on Space THz Tech.*—Pasadena, California, Mar. 1998, pp. 563-572.

S.H. Wang et al., PowerPoint presentation entitled "T-Ray Imaging," *IEEE IMS 2003 WFC Workshop Talk: Sensing Science and Electronic Technology at Terahertz Frequencies*—Philadeplphia, Pennsylvania, Jun. 2003, 46 pages in length.

G. Davies et al., "Invited—Terahertz Quantum Cascade Lasers," *IEEE MTT-S Digest—Int. Microwave Sym., EW5A-2*, Philadelphia, Pennsylvania, Jun. 8-13, 2003, pp. 743-746.

R. Rüdiger et al., "All-Solid-State Radiometers for Environmental Studies to 700 GHz," *Proceedings of the 3rd International Symposium on Space Terahertz Technology*, Jun. 2000, pp. 706-723.

\* cited by examiner

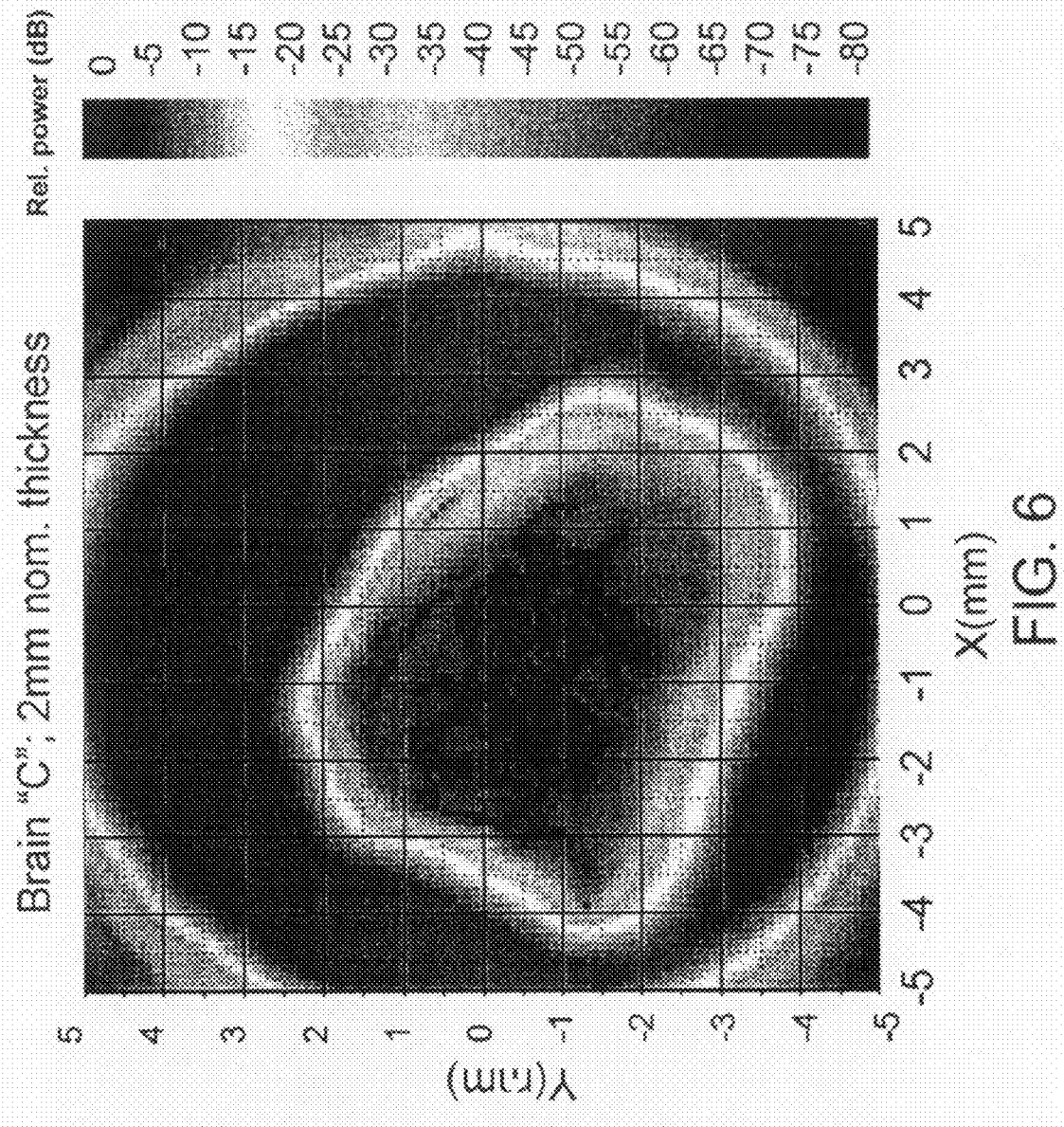

SUB-MILLIMETER WAVE FREQUENCY HETERODYNE DETECTOR SYSTEM

PRIORITY CLAIM

This application is a continuation of U.S. application Ser. No. 10/956,734, filed Oct. 1, 2004, now U.S. Pat. No. 7,507,963, which claims the benefit of Provisional Application No. 60/507,980, filed Oct. 1, 2003.

STATEMENT OF GOVERNMENT INTEREST

This invention described herein was made in the performance of work under a NASA contract, and is subject to the provisions of Public Law 96-517 (35 USC 202) in which the Contractor has elected to retain title.

BACKGROUND OF THE INVENTION (1) Technical Field

The present invention relates to a sub-millimeter wave frequency heterodyne imaging system. More specifically, the present invention relates to a sub-millimeter wave frequency heterodyne detector system for imaging the magnitude and phase of transmitted power through or reflected power off of mechanically scanned samples at sub-millimeter wave frequencies.

(2) Background

A wealth of useful spectral information exists at sub-millimeter wave frequencies: 300 GHz-3000 GHz (wavelengths from 1 millimeter (mm) to 100 microns). Astronomers have long pursued programs to develop this technology for Earth, planetary and space science applications; and recently, the biological and biomedical areas have begun pursuing the same technology. However, the same properties that make the sub-millimeter wave frequencies so interesting—high absorption and emission from many gaseous species, liquids and solids (especially water)—make it extremely difficult for significant penetration or propagation of terahertz energy, thus severely limiting imaging, radar and communications applications.

One current method of examining biological and other material samples is through the use of ultra-fast pulse time-domain spectroscopy (TDS). This technique yields wide spectral coverage, but has limited frequency resolution and signal-to-noise ratio. TDS also has limited penetration depth in lossy samples such as wet tissue, where measured penetration depth is generally on the order of a few microns. For any transmission application, the losses due to water absorption are untenably high; measured at an absorption coefficient of 450 $cm^{-1}$ at 2.5 terahertz. Thus, the applicability of TDS to biological materials is limited.

Additionally, the Fourier Transform Spectroscopy (FTS) method has also been implemented for measuring biological materials. While FTS is more sensitive and has a much shorter sampling time than traditional spectroscopy techniques, it is again limited in its dynamic range and spectral resolution. For applicability to biological materials, it is similar to TDS—possessing a penetration depth of only microns in wet tissue.

Therefore, a need exists in the art for a sub-millimeter wave frequency detector system with increased dynamic range and measurement capability. Specifically, an imaging system that can measure weak signals through very lossy samples is desirable.

SUMMARY OF THE INVENTION

The present invention provides a system and a method that overcomes the aforementioned limitations and fills the aforementioned needs by providing a sub-millimeter wave frequency heterodyne detector system for imaging the magnitude and phase of transmitted power through or reflected power off of mechanically scanned samples at sub-millimeter wave frequencies. The system comprises a signal source and a local oscillator source, both operating at a sub-millimeter wave frequency. Further, in one embodiment, a sub-millimeter wave frequency mixer feeds an intermediate frequency to a spectrum analyzer, which is then translated into an image for a user.

In one aspect of the invention, a sub-millimeter wave frequency heterodyne detector system comprises a first sub-millimeter wave frequency signal beam originating from a first signal source, wherein the first signal beam passes through a sample and into a mixer; and a second sub-millimeter wave frequency signal beam originating from a second signal source and functioning as a local oscillator, wherein the first signal beam and second signal beam pass into the mixer and downconvert into an intermediate frequency output.

In another aspect of the invention, a computer controls the X and Y position of a sample surface, stores the position data and combines the position data with image data from a spectrum analyzer and converts the data into a viewable image.

In a further aspect, the sub-millimeter wave frequency is 2.523 terahertz (THz).

In a yet further aspect, the first signal source is an optically pumped far infrared laser.

In another aspect, the laser line is methanol ($CH_3OH$).

In still another aspect of the invention, the laser operates at a frequency of 2.523 THz.

In another aspect of the invention, the first signal source supplies up to 70 milliwatts (mW).

In a further aspect, the second signal source is an optically pumped far infrared laser.

In a yet further aspect, the laser line is $CH_3OH$.

In another aspect of the invention, the laser line is difluoromethane ($CH_2F_2$).

The signal source of Claim 10, wherein the laser operates at a frequency of 2.523 THz.

In a further aspect, the sample is any form of matter desired for measurement of sub-millimeter wave frequency penetration.

In another aspect of the invention, the first signal beam passes from the first signal source through a first focusing lens before passing through the sample, and wherein the signal beam passes from the sample through a second lens to enlarge the signal beam.

In another aspect of the invention, the first signal diameter is focused from 3 millimeters to 1 millimeter before passing through the sample.

In a yet further aspect, the lens is a Teflon® (polytetrafluoroethylene) lens.

In a further aspect, the mixer is a 2.523 THz planar GaAs Schottky diode mixer.

In another aspect of the invention, a spectrum analyzer receives the intermediate frequency output from the mixer and acts as a power detector and phase detector to produce image data.

In another aspect of the invention, a sub-millimeter wave frequency heterodyne detector system comprising a first terahertz frequency signal beam originating from a first signal source, wherein the first signal beam passes through a sample and into a mixer; a second terahertz frequency signal beam originating from a second signal source and functioning as a local oscillator, wherein the first signal beam and second signal beam pass into the mixer and downconvert into an intermediate frequency output; and a computer which control the X and Y position of a sample surface, stores the position data and combines the position data with the image data into a viewable image.

In a further aspect, a method of forming a sub-millimeter wave frequency heterodyne detector system, the method comprising the acts of sending a first sub-millimeter wave frequency signal beam originating from a first signal source, wherein the first signal beam passes through a sample and into a mixer; and sending a second sub-millimeter wave frequency signal beam originating from a second signal source and functioning as a local oscillator, wherein the first signal beam and second signal beam pass into the mixer and downconvert into an intermediate frequency output.

In another aspect of the invention, the act of forming the sub-millimeter wave frequency heterodyne detector system comprises the act of using a computer to control the X and Y position of a sample surface, store the position data and combine the position data with image data from a spectrum analyzer to convert the data into a viewable image.

In a yet further aspect, the sub-millimeter wave frequency is 2.523 terahertz (THz).

In a further aspect, the first signal source is an optically pumped far infrared laser.

In another aspect of the invention, the laser line is methanol ($CH_3OH$).

In a yet further aspect, the laser operates at a frequency of 2.523 THz.

In a further aspect, the method comprises a first signal source supplies up to 70 milliwatts (mW).

In another aspect of the invention, the second signal source is an optically pumped far infrared laser.

In a yet further aspect, the laser line is $CH_3OH$.

In a yet further aspect, the laser line is difluoromethane ($CH_2F_2$).

In another aspect of the invention, the laser operates at a frequency of 2.523 THz.

In another aspect of the invention, the sample is any form of matter desired for measurement of sub-millimeter wave frequency penetration.

In a further aspect, the act of passing a signal beam through a sample further comprises the acts of passing a first signal beam from the first signal source through a first focusing lens before passing through the sample, and passing the signal beam from the sample through a second lens to enlarge the signal beam.

In another aspect of the invention, the act of passing a signal beam through a sample further comprises the acts of focusing the first signal diameter from 3 millimeters to 1 millimeter before passing through the sample.

In another aspect of the invention, the lens is a Teflon® (polytetrafluoroethylene) lens.

In a further aspect, the mixer is a 2.523 THz planar GaAs Schottky diode mixer.

In a further aspect, the method using a spectrum analyzer to create a viewable image comprises the additional acts of:
  receiving the intermediate frequency output from the mixer and acting as a power detector and phase detector by producing image data.

In another aspect of the invention, a method of forming a sub-millimeter wave frequency heterodyne detector system, the method comprising the acts of sending a first sub-millimeter wave frequency signal beam originating from a first signal source, wherein the first signal beam passes through a sample and into a mixer; sending a second sub-millimeter wave frequency signal beam originating from a second signal source and functioning as a local oscillator, wherein the first signal beam and second signal beam pass into the mixer and downconvert into an intermediate frequency output; and using a computer to control the X and Y position of a sample surface, store the position data and combine the position data with image data from a spectrum analyzer to convert the data into a viewable image.

BRIEF DESCRIPTION OF THE DRAWINGS

The objects, features and advantages of the present invention will be apparent from the following detailed descriptions of the preferred aspect of the invention in conjunction with reference to the following drawings, where:

FIG. 6 is a graphic illustration of an image produced by the heterodyne imaging system.

DETAILED DESCRIPTION

Figure 1:
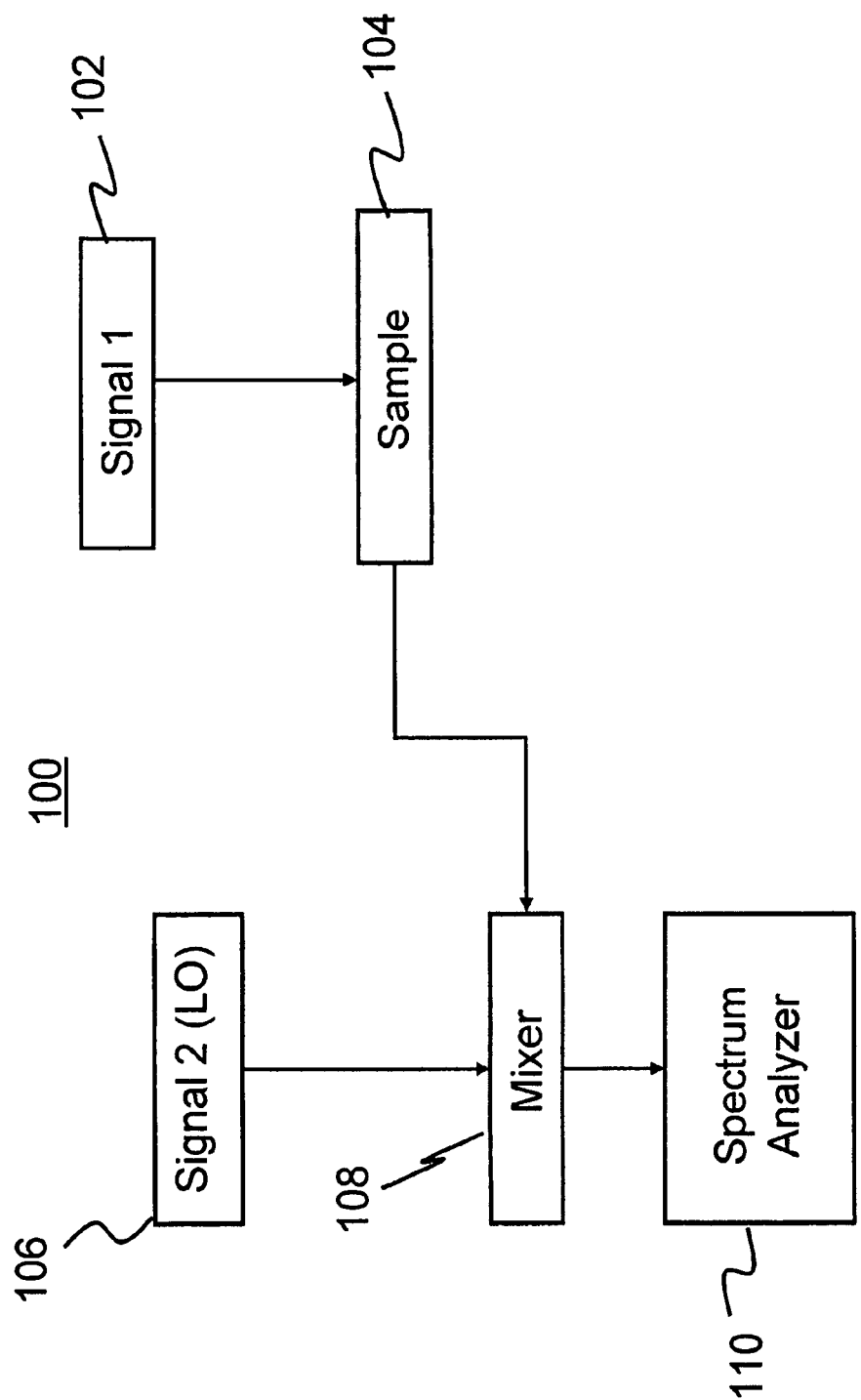
FIG. 1 depicts a block diagram of one embodiment of a sub-millimeter wave frequency heterodyne detector system, representing the steps taken from the origin of a signal source to an image capture.

The present invention relates to sub-millimeter wave frequency heterodyne detector systems. More specifically, the present invention relates to a system and method for imaging the transmission loss and phase of thin samples using a sub-millimeter wave frequency heterodyne detector. The following description, taken in conjunction with the referenced drawings, is presented to enable one of ordinary skill in the art to make and use the invention and to incorporate it in the context of particular applications. Various modifications, as well as a variety of uses in different applications, will be readily apparent to those skilled in the art, and the general principles, defined herein, may be applied to a wide range of embodiments. Thus, the present invention is not intended to be limited to the embodiments presented, but is to be accorded the widest scope consistent with the principles and novel features disclosed herein. Furthermore, it should be noted that unless explicitly stated otherwise, the figures included herein are illustrated diagrammatically and without any specific scale, as they are provided as qualitative illustrations of the concept of the present invention.

(1) Introduction

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The description outlined below sets forth a sub-millimeter wave frequency heterodyne detector system and imager. More specifically, the description sets forth a system for imaging the magnitude and phase of transmitted power through or reflected power off of mechanically scanned samples at sub-millimeter wave frequencies.

The sub-millimeter wave frequency heterodyne detector system can successfully and accurately measure weak signals through samples that would otherwise be unpenetrable using traditional sub-millimeter wave detector techniques.

Continuous wave (CW) heterodyne imaging offers extremely large dynamic range and high signal-to-noise ratio while maintaining fast data acquisition, stable magnitude and phase measurements, reasonable frequency flexibility and millimeter-scale penetration in wet tissues and other biological materials. To achieve a desirable level of penetration, a strong sub-millimeter illumination signal and close frequency-spaced oscillator source is needed.

The sub-millimeter wave frequency heterodyne imaging system has demonstrated, in one embodiment, penetration of more than 2 millimeters (mm) at 2.523 terahertz (THz). At this penetration depth, applications include: establishing contrast mechanisms in biological and electronic applications; two and three dimensional transmission/reflection imaging; pump-probe resonance in liquids and solids; radiation-induced effects in biomaterials; change of state measurements; and radiometric imaging of subjects in-vivo. Applications are possible over a range of sub-millimeter wave frequencies, and have been demonstrated in a range from 300 GHz-3000 GHz.

In one embodiment of the sub-millimeter wave frequency heterodyne detector system, two signal sources are used; one signal source acting as the signal beam which scans the sample, while a second signal source acts as a local oscillator (LO) source for a mixer. The mixer provides a workable intermediate frequency (IF) output. The IF output is then passed to a spectrum analyzer where the measured transmission or reflection of a target sample is displayed as an image.

In another embodiment of the sub-millimeter wave frequency heterodyne detector system comprises two signal sources, two mixers, and an intermediate frequency tracking system. A signal from the first source is used for measuring a sample, while a signal from the second source is used as a local oscillator (LO) for two mixers. A reference mixer receives inputs from both the signal source and the LO source. A signal mixer receives an input from the LO source and the first source after it has been effected by the sample. The mixers feed the mixed signals into an intermediate frequency (IF) tracking system. The IF tracking system uses an additional LO and a lock-in amplifier to identify the desired signal, after which the signal is processed into an image using the data provided by the lock-in amplifier and the position data from the scanned sample. The position data is fed to the controlling computer from a separate motion controller connected to the computer via General Purpose Interface Bus (GPIB) interface. The motion controller directly drives the X and Y linear motorized stages, where the sample may be placed.

(2) Definitions

In order to provide a working frame of reference, first a glossary of some of the terms used in the description and claims is given as a central resource for the reader. The glossary is intended to provide the reader with a general understanding of various terms as they are used in this disclosure, and is not intended to limit the scope of these terms. Rather, the scope of the terms is intended to be construed with reference to this disclosure as a whole and with respect to the claims below.

Before describing the specific details of the present invention, it is useful to provide a centralized location for various terms used herein and in the claims. A definition has been included for these various terms. However, the definition provided should not be considered limiting to the extent that the terms are known in the art. These definitions are provided to assist in the understanding of the present invention.

Heterodyne—To generate new frequencies by mixing two or more signals in a nonlinear device such as a vacuum tube, transistor, or diode mixer.

Etalon—An optical filter that uses a pair of semi-reflecting, semi-transmissive parallel surfaces to create resonance via multiple-beam interference between the surfaces.

Mixer—A device for combining two signals non-linearly to produce sum and/or difference signals.

(3) Details

A. Sub-millimeter Wave Frequency Heterodyne Detector System

In one embodiment, the sub-millimeter wave frequency heterodyne detector system is based on a sub-millimeter wave mixer and two signal sources. FIG. 1 presents a block diagram representing the components of a simple heterodyne imaging system 100 and the steps taken to create a viewable image. One signal source 102 is the signal beam, which scans the sample 104, while the second signal source 106 acts as a local oscillator (LO) source for the mixer 108. The mixer 108 provides a workable intermediate frequency (IF) output. The IF signal is then passed to a spectrum analyzer 110 where the measured transmission or reflection of a target sample is displayed as an image.

Figure 2:
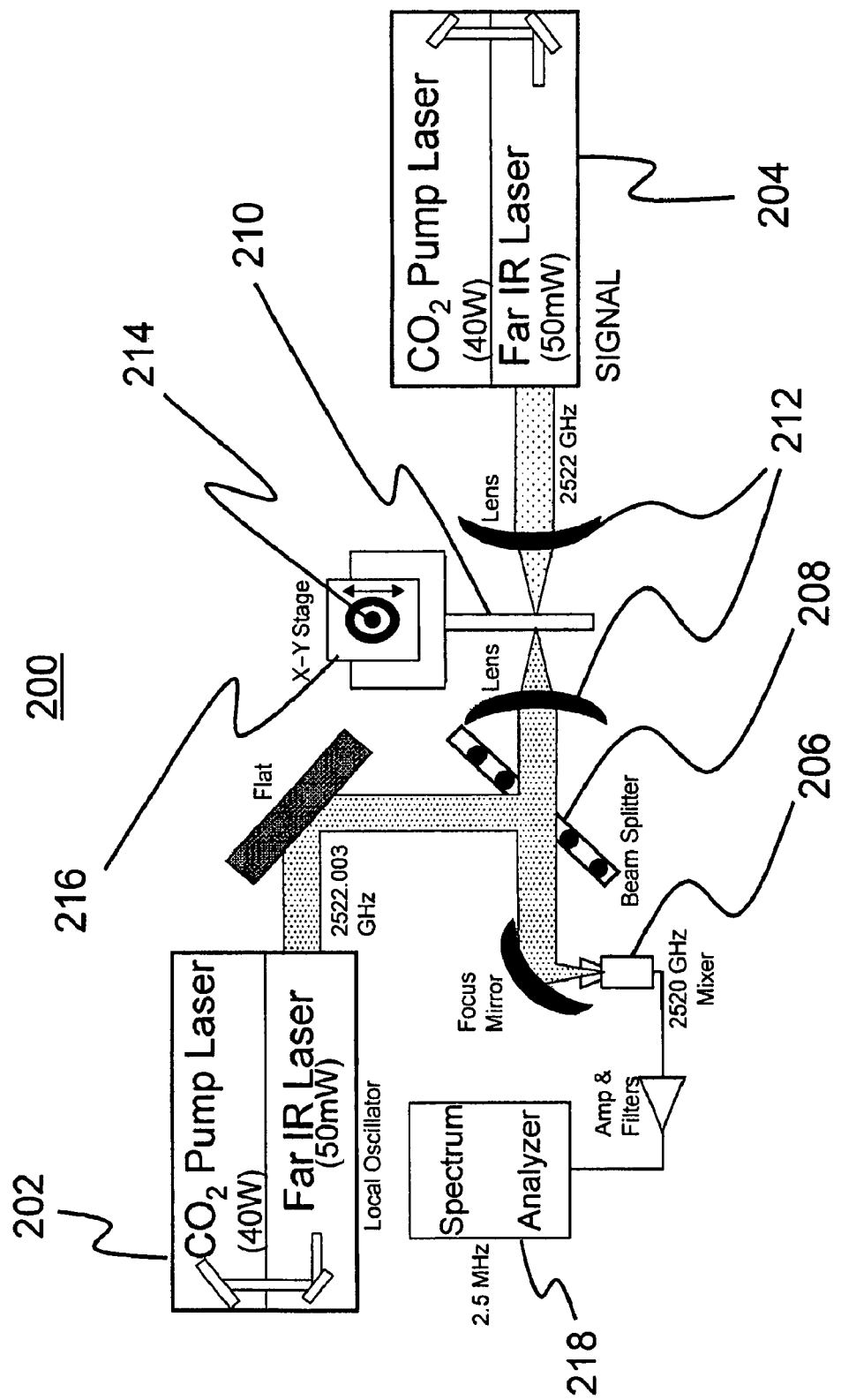
FIG. 2 depicts a detailed diagram of one embodiment of a heterodyne detector system, representing the steps taken from the origin of a signal source to an image capture.

A more detailed illustration of one embodiment of the simple heterodyne detector system, as illustrated by the diagram in FIG. 2. A sub-millimeter wave frequency heterodyne detector system 200 comprises two commercially available optically pumped carbon dioxide ($CO_2$) far-infrared (IR) lasers (manufactured by Coherent, Inc., Santa Clara, Calif.). Both lasers are operated on the 118.83 micrometer (EM) methanol ($CH_3OH$) line but at slightly different frequencies (e.g., 2522 GHz and 2522.003 GHz as seen in FIG. 2). One laser 204 is used for the signal beam to scan a sample, while the second laser 202 acts as a local oscillator (LO) source. The two lines then feed into a 2.523 terahertz (THz) planar gallium arsenic (GaAs) Schottky diode mixer 206 via a beam splitter 208. The LO laser 202 is fed straight into the mixer, while the signal laser 204 beam is focused down from its nominal 3 millimeter (mm) diameter to roughly 1 mm at the sample plane 210 using a pair of Teflon® (polytetrafluoroethylene) lenses 212 (available from Dupont Corp., Wilmington, Del.). The sample 214 is moved in a plane normal to the beam using a computer controlled X-Y stage 216. The position data is fed to the controlling computer (not shown) from a separate motion controller connected to the computer via a General Purpose Interface Bus (GPIB) interface (also not shown). The motion controller directly drives the X and Y linear positions of the motorized stages. The mixer 206 provides an IF output to an Agilent E4408 spectrum analyzer 218 (Agilent Technologies, Inc., Palo Alto, Calif.), which serves as the imaging device to produce a viewable image. With the embodiment described, experiments resulted in a dynamic range of 60 decibels (dB) giving a penetration depth of 1 millimeter (mm) in tissue, amplitude resolution 0.2 dB, and an acquisition rate of 5 pixels per second (limited by the particular spectrum analyzer in this embodiment).

In the aforementioned embodiment, commercial carbon dioxide-pumped far infrared lasers and high-sensitivity room temperature THz planar Schottky diode mixers are used to create a THz heterodyne detector system. However, one skilled in the art will appreciate that a variety of other types of signal sources and mixers are available. Sensitivity enhancement is possible (at the expense of high-end dynamic range) by replacing the Schottky mixer with a more sensitive hot electron bolometer or superconductor-insulator-superconductor element. Factors of 10-100 in low-end signal acquisition are possible with these near-quantum limited receiver elements. Additionally, significant improvement in frequency agility could be achieved by replacing the two far IR lasers with semiconductor cascade lasers.

One skilled in the art will also appreciate that operation of the detector system at other sub-millimeter wave frequencies is possible by the judicious choice of laser lines and replacement of the Schottky diode mixer with downconverters optimized for the different frequencies. Additionally, one skilled in the art will also appreciate that other lenses or focusing devices can be used to focus the signal beam before passing through the sample.

B. Phase-Stabilized Sub-Millimeter Wave Frequency Heterodyne Detector System

In another embodiment, improved dynamic range and frequency stability can be obtained with a more complex arrangement, whereby the intermediate frequency (IF) signal to be detected is essentially phase-stabilized against itself.

Figure 3:
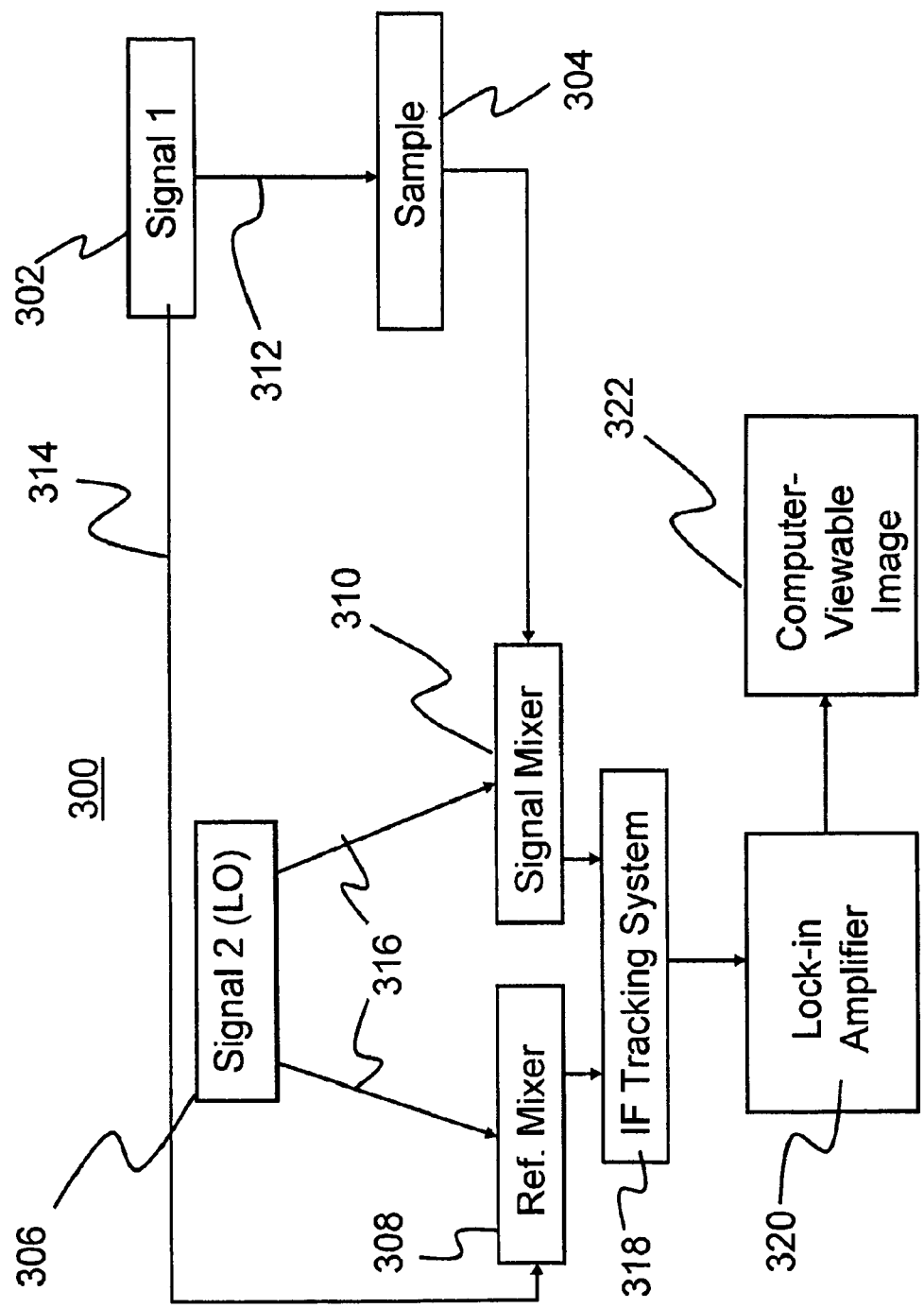
FIG. 3 depicts a block diagram of one embodiment of a phase-stabilized sub-millimeter wave frequency detector system, including a reference mixer and signal mixer, an intermediate frequency tracking system, and a lock-in amplifier.

The phase-stabilized heterodyne detector system is based on two sub-millimeter wave mixers and two signal sources. FIG. 3 presents a block diagram representing the components of one embodiment of a phase-stabilized system 300. In this embodiment, one signal source 302 is the signal beam, which scans the sample 304, while the second signal source 306 acts as a local oscillator (LO) source for two mixers, a reference mixer 308 and signal mixer 310. The signal from the first signal source 302 is divided into a measurement path 312 and reference path 314 and is mixed in each mixer with the same LO signal 316 derived from the second signal LO signal source 306. This results in two IF signals that are equal in instantaneous frequency but differ in amplitude and phase.

The mixers 308 and 310 each provide a mixed signal to an intermediate frequency (IF) tracking system 318, which acts as the primary detector and produces a workable IF output. The system 300 uses the reference mixer 308 along with the IF tracking system and a lock-in amplifier 320 to monitor and normalize the signal sources 302 and 306. The spectrum analyzer of the previously described embodiment is replaced with the lock-in amplifier 320 to maximize throughput. The IF tracking system 318 passes the signal through the lock-in amplifier 320 to identify the desired signal, where the measured transmission or reflection of a target sample 304 is then displayed as an image 322.

Figure 4:
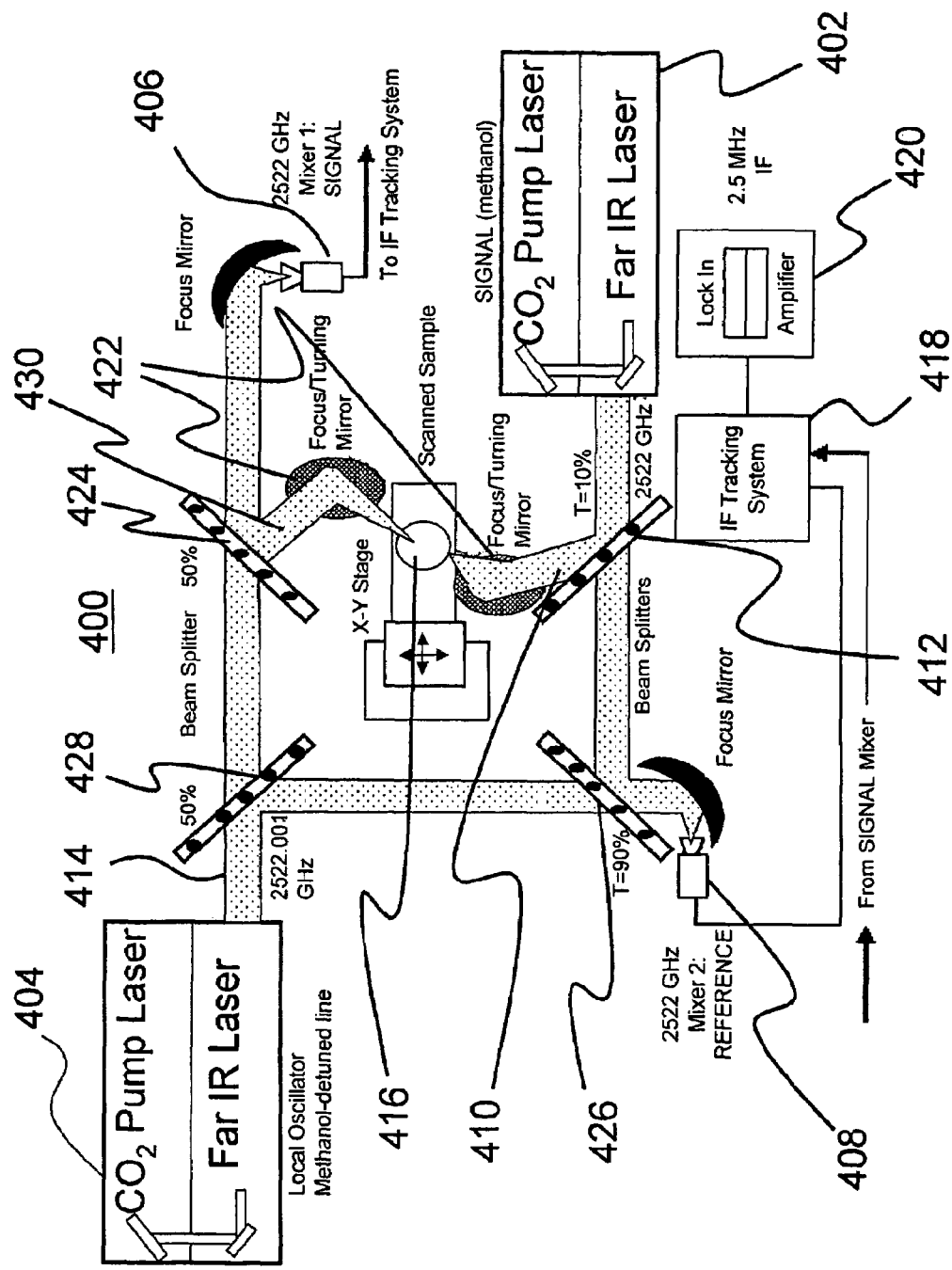
FIG. 4 depicts a detailed diagram of one embodiment of a phase-stabilized sub-millimeter wave frequency detector system, including a reference mixer and signal mixer, an intermediate frequency tracking system, and a lock-in amplifier.

In one embodiment, as illustrated by the diagram in FIG. 4, a sub-millimeter wave frequency heterodyne detector system 400 comprises two commercially available carbon dioxide ($CO_2$) optically pumped far IR lasers. One laser 402 is used for the signal beam to scan a sample 416, and supplies as much as 70 milliwatts (mW) at 2.523 Terahertz (THz). The second laser 404 acts as a LO source for two mixers 406 and 408. The two lasers operate at slightly different frequencies (e.g., 2522 GHz and 2522.001 GHz as seen in FIG. 4). In the present embodiment, the system 400 is based around the two high-sensitivity room temperature 2.523 THz Schottky diode mixers; a measurement mixer 406 and reference mixer 408. The beam 410 from the signal laser 402 is split into measurement and reference paths via a beam splitter 412, and is mixed in each mixer using the same LO signal 414 derived from the second laser 404. The beam 410 from the signal laser 402 passes through the sample 416 and then into the measurement mixer 406. A second input into the measurement mixer 406 is a portion of the beam 414 from the LO laser 404. A portion of the beams 410 and 414 from both lasers also passes into the reference mixer 408. The output of each mixer passes into an IF tracking system 418 to produce a workable IF output of 24 GHz. The resulting IF output is then passed through a lock-in amplifier 420 to isolate the desired frequency, after which a viewable image may be obtained.

In one embodiment, in order to maximize throughput, the spectrum analyzer 218 depicted in FIG. 2 is be replaced with a Stanford Research SR844 RF lock-in amplifier (LIA) 420, (Stanford Research Systems, Sunnyvale, Calif.). In addition to having a maximum 2 millisecond latency between the issuance of a trigger command to it and the actual logging of data, the LIA can also measure the relative phase difference between the reference and measurement IF signals, thereby providing phase delay imagery of the samples. In order to improve the spatial resolution of the imaging system and reduce optics losses by roughly 20 dB, the Teflon (polytetrafluoroethylene) lenses originally used to focus the signal beam before hitting the sample can be replaced with a pair of off-axis parabolic mirrors 422. This change reduced the beam diameter to less than 0.55 mm.

One skilled in the art will appreciate that there are many different frequency stabilization schemes that may be employed to track and calibrate the two sub-millimeter lasers. In this embodiment, stability of roughly 0.1 decibels (dB) and less than 5 degrees have been achieved with a dynamic range of more than 110 dB. The present system scans the sample through the focused beam and measures transmission or reflection at a fixed radio frequency (RF). Penetration in wet tissue is more than 2 mm at 2.523 THz.

Broader RF bandwidth is possible with tunable signal sources and wider IF band amplifiers. In order to achieve optimal signal-to-noise ratio (S/N), the pre-detection bandwidth should be made as narrow as possible. However, in order to obtain an image of reasonable resolution (many scanned pixels), it is desirable to use the largest possible pre-detection bandwidth so as to minimize the image acquisition time. The pre-detection bandwidth should therefore be selected to optimize the particular requirements of a specific application. In addition to these conflicting requirements, there is the added complication of the stability of the submillimeter wave sources (better than 1 part in $10^9$ is required; i.e., within 3 kHz). The minimum frequency drift of the commercial carbon dioxide ($CO_2$) pumped far IR lasers over a 5 minute period is about 150 kHz. Bearing these limitations in mind, a system for imaging the transmission loss and phase of thin (less than 10 mm thick) biosamples at 2.523 THz has been constructed and successfully tested in the laboratory. Dynamic range as great as 110 dB has been measured with a 3 dB pixel size of less than 0.4 mm. The noise in the phase measurements is less than +/−2 degrees.

Operation at frequencies other than 2.523 THz is possible by judicious choice of laser lines and replacement of the two Schottky diode mixers with mixers optimized for the different frequencies. Sensitivity enhancement is also possible (at the expense of high end dynamic range) by replacing the Schottky mixers with more sensitive hot electron bolometer or superconductor-insulator-superconductor elements. Factors of 1000 in low-end signal acquisition are possible with these near quantum-limited receiver elements. Finally, significant improvement in frequency agility can be achieved by replacing the two far IR lasers with recently available semiconductor quantum cascade lasers.

In another embodiment, the detuned methanol ($CH_3OH$) LO laser 404 is operated with difluouromethane ($CH_2F_2$) lasing at 2546 GHz, yielding an IF frequency of 24 GHz. The wider IF allows even better frequency stabilization and enhanced noise performance from the two mixers. In an additional embodiment, two beam splitters 424 and 426 are replaced with frequency diplexing silicon etalons. The diplexing etalons isolate the measurement signal path from the LO laser by greatly reducing the amount of measurement signal reflected back from the reference mixer into the LO laser path. The etalons are designed for almost perfect transmission (over 99%) at the 2.523 THz RF frequency, so nearly all of the signal reflected back from the reference mixer at that frequency will pass back through the etalon and back into the RF laser instead of being reflected into the LO laser path. What little RF signal does get to the LO laser and is back-reflected toward the measurement mixer passes through the diplexing etalon at that mixer instead of being reflected into it. As a result a dynamic range in excess of 110 dB is possible with this system.

In the tracking circuit, due to the large amount of available power at the lasers (about 60 mW) and the excellent performance of the THz mixers, attenuation is added in front of the reference mixer 408 and LO laser 404 to provide effective isolation without significantly degrading the performance of the measurement mixer 406. Combining this method with replacement of one of the beam-splitting polarizing grids 428 with a Mylar® (biaxially-oriented polyethylene terephthalate) beam splitter (to reduce stray coupling from specular reflection of the grid wires) increased the dynamic range to about 75 dB (Mylar is a registered trademark of Dupont Corp., Wilmington, Del.). By carefully adjusting the position of the reference mixer 408 to provide some phase cancellation of the stray measurement signal 430, another 10 to 15 dB of measurement range can be obtained.

C. Tracking/Detector System

Figure 5:
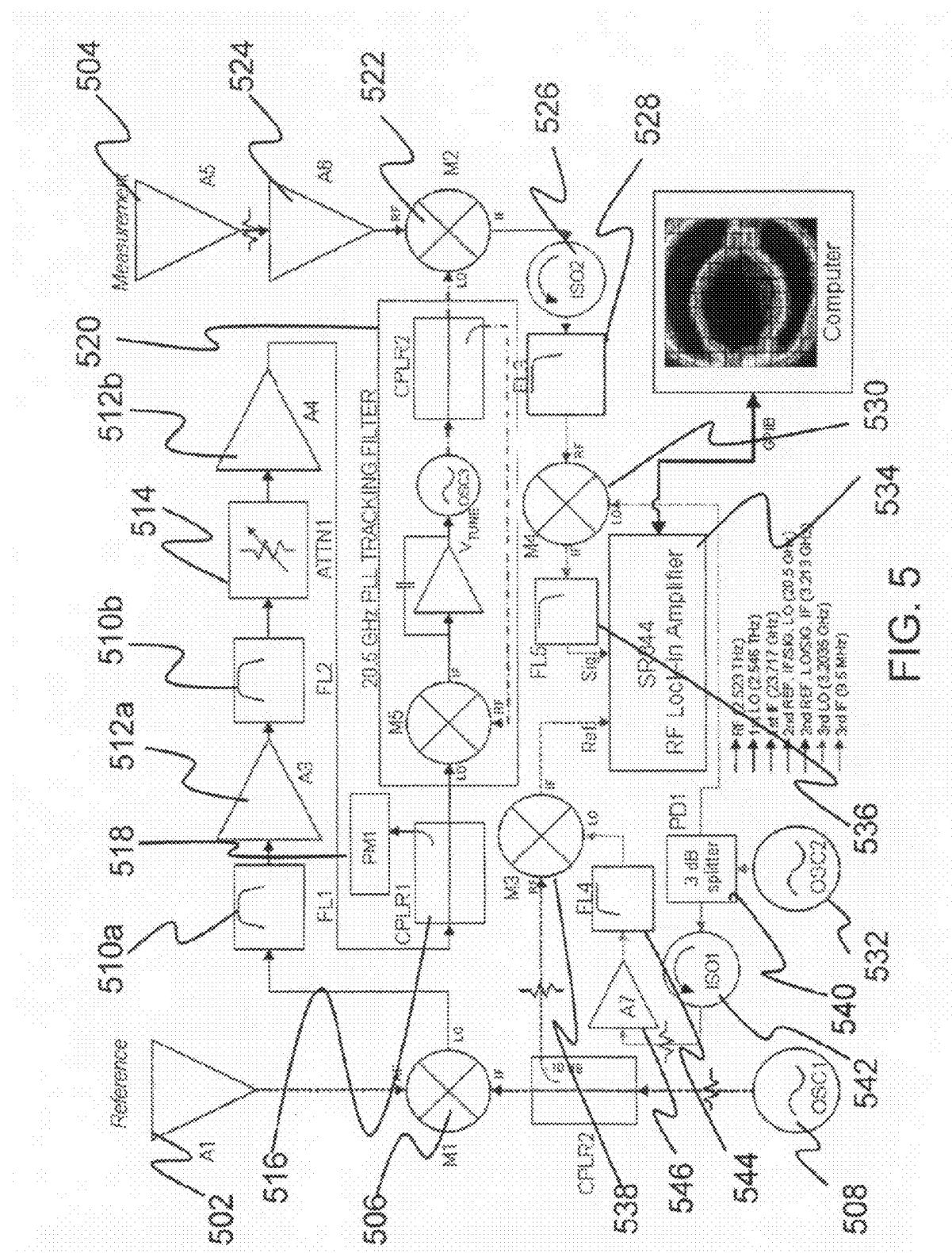
FIG. 5 depicts a detailed circuit design for the IF tracking system, representing the input of a signal mixer and reference mixer and the output of an intermediate frequency to a lock-in amplifier.

In one embodiment, as illustrated in FIG. 5, microwave (23.7 GHz) IF signals from the reference 408 and measurement 406 THz mixers (shown in FIG. 4) are applied to microwave amplifiers 502 and 504 respectively. The amplified reference IF signal from the amplifier 502 is applied to a first mixer 506, which is pumped by a relatively low frequency (~3.2 GHz) signal from a first oscillator 508 via the IF port of mixer 506. The 20.5 GHz output of mixer 506 is taken at its LO port and is heavily bandpass filtered (to remove the undesired sideband from the mixer 506) and amplified by bandpass filters FL1 510a, FL2 510b, and amplifiers A3 512a and A4 512b. An attenuator 514 controls the amount of gain in this path. The signal passes through a directional coupler 516 for sampling by the microwave power meter 518 and is applied to the 20.5 GHz phase-locked loop (PLL) tracking filter 520.

The tracking filter 520 serves as a very narrow bandpass filter (~1 MHz bandwidth), passing only the downconverted linewidth of the THz lasers to the LO port of a second mixer 522. The RF port of the second mixer 522 is fed with the amplified measurement IF signal from microwave amplifiers 504 and 524. The 3.2 GHz IF output of the second mixer 522 is fed through an isolator 526 and a low pass filter 528 to the RF port of a third mixer 530. The third mixer 530 is pumped by a second oscillator 532 operating at a slightly different frequency than the first oscillator 508 so as to produce an IF frequency that can be readily detected by the RF lock-in amplifier 534 (in one embodiment, 9.5 MHz, so the frequency of the second oscillator 532 is 3.2095 GHz). The 9.5 MHz IF output of the third mixer 530 is fed through a low pass filter 536 to the signal input of the RF lock-in amplifier 534. The 9.5 MHz reference signal for the RF lock-in amplifier 534 is generated by mixing the first oscillator 508 and second oscillator 532 in a fourth mixer 538. A 3 dB splitter 540, an isolator 542, and high pass filter 544 provide the high amount of isolation required to prevent stray 3.2 GHz or 9.5 MHz signals from reaching the LO port of the fourth mixer 538 which would result in crosstalk, reducing the dynamic range of the system. An amplifier 546 boosts the level of the second oscillator 532 to the LO drive power required by a fourth oscillator (not shown).

D. Imager

The RF lock-in amplifier measures the magnitude of the signal at its signal input, and compares its phase with the phase of the reference signal. Measurement is triggered by a command sent from the control computer, and is stored in memory in the lock-in amplifier 534 (also 420 in FIG. 4). The sample to be imaged is placed in an X-Y translation stage, and the computer commands the stage to move the sample through the THz imaging beam in a raster pattern. As the sample is passed through the beam, the computer triggers the lock-in amplifier to acquire data at linear intervals specified by the user. Blocks of data are periodically read from the LIA by the computer during translation stage queuing and are stored and displayed.

The imager acquires vector data from the LIA and combines this data with position data from X and Y positioners in the controlling computer and stored on the computer in text files in simple "XYZ" format (X position, Y position, and Z vector magnitude/phase data). In real time, a computer program displays this data during acquisition by assigning colors to different power levels and phases and plotting the points as a two dimensional raster image. A typical image is represented in FIG. 6, where the relative power is plotted against position of the beam with respect to the sample.

What is claimed is:

1. A method of imaging a sample comprising the steps of:
generating a signal beam of optical radiation having a frequency between 300 and 3000 gigahertz;

generating a reference beam of optical radiation having a frequency between 300 and 3000 gigahertz and different from the signal beam;

splitting the signal beam into first and second portions and causing the first portion of the beam to be scanned with respect to the sample;

splitting the reference beam into first and second portions;

mixing the first portion of the signal beam that has interacted with the sample with the first potion of the reference beam to create a measurement intermediate frequency signal;

mixing the second portion of the signal beam and the second portion of the reference beam to create a reference intermediate frequency signal; and processing the measurement and reference intermediate frequency signals in order to derive magnitude and phase information as a function of position of the first portion of the signal beam on the sample and either storing the information or displaying the information in the form of an image.

2. A method as recited in claim 1, wherein said phase information is derived by determining the relative phase difference between the measurement and reference intermediate frequency signals.

3. A method as recited in claim 1, wherein said processing step includes feeding the measurement and reference intermediate frequency signals into a lock-in amplifier.

4. A method as recited in claim 1, wherein said first portion of the signal beam is laterally scanning with respect to the sample to permit generation of two-dimensional image information.

5. A method as recited in claim 4, wherein the two dimensional image information is displayed.

6. A method as recited in claim 5, wherein the displayed image information is relative power as a function of scan position.

7. A method as recited in claim 1, wherein said signal and reference beams are generated by optically pumped far infrared lasers.

8. A method as recited in claim 1, wherein said signal and reference beams are generated by quantum cascade lasers.

9. A method as recited in claim 1, wherein the signal beam interacts with the sample through transmission.

10. A method as recited in claim 1, wherein said signal beam interacts with the sample by reflection.

11. A method as recited in claim 1, wherein the sample is a biological sample.

12. A system for imaging a sample comprising:
a first generator for generating a signal beam of optical radiation having a frequency between 300 and 3000 gigahertz;
a second generator for generating a reference beam of optical radiation, having a frequency between 300 and 3000 gigahertz that is different from the signal beam;
a first beam splitter for dividing the signal beam into first and second portions;
means for scanning the first portion of the signal beam with respect to the sample;
a second beam splitter for dividing the reference beam into first and second portions;
a first mixer for mixing the first portion of the signal beam after interaction with the sample with the first potion of the reference beam to create a measurement intermediate frequency signal;
a second mixer for mixing the second portion of the signal beam and the second portion of the reference beam to create a reference intermediate frequency signal; and
a processor for processing the measurement and reference intermediate frequency signals in order to derive magnitude and phase information as a function of position of the first portion of the signal beam on the sample, said magnitude and phase information capable of being converted into image information.

13. A system as recited in claim 12, wherein the processor functions to determine the relative phase difference between the measurement and reference intermediate frequency signals.

14. A system as recited in claim 12, wherein the processor includes a lock-in amplifier.

15. A system as recited in claim 12, wherein said scanning means laterally scans the first portion of the signal beam with respect to the sample to generate two-dimensional image information.

16. A system as recited in claim 15, further including a display for displaying the two dimensional image information.

17. A system as recited in claim 16, wherein the displayed image information is relative power as a function of scan position.

18. A system as recited in claim 12, wherein the generators are optically pumped far infrared lasers.

19. A system as recited in claim 12, wherein the generators are quantum cascade lasers.

20. A system as recited in claim 12, wherein the signal beam interacts with the sample through transmission.

21. A system as recited in claim 12, wherein said signal beam interacts with the sample by reflection.

22. A method of imaging a sample comprising the steps of:
generating a submillimeter wave frequency optical radiation signal beam;
generating a submillimeter wave frequency optical radiation reference beam having a frequency different from the signal beam;
splitting the signal beam into first and second portions and causing the first portion of the beam to be scanned with respect to the sample;
splitting the reference beam into first and second portions;
mixing the first portion of the signal beam that has interacted with the sample with the first potion of the reference beam to create a measurement intermediate frequency signal;
mixing the second portion of the signal beam and the second portion of the reference beam to create a reference intermediate frequency signal; and
processing the measurement and reference intermediate frequency signals in order to derive magnitude and phase information as a function of position of the first portion of the signal beam on the sample and either storing the information or displaying the information in the form of an image.

23. A method as recited in claim 22, wherein said phase information is derived by determining the relative phase difference between the measurement and reference intermediate frequency signals.

24. A method as recited in claim 22, wherein said processing step includes feeding the measurement and reference intermediate frequency signals into a lock-in amplifier.

25. A method as recited in claim 22, wherein said first portion of the signal beam is laterally scanning with respect to the sample to permit generation of two-dimensional image information.

26. A method as recited in claim 25, wherein the two dimensional image information is displayed.

27. A method as recited in claim 26, wherein the displayed image information is relative power as a function of scan position.

28. A method as recited in claim 22, wherein the signal beam interacts with the sample through transmission.

29. A method as recited in claim 22, wherein said signal beam interacts with the sample by reflection.

30. A system for imaging a sample comprising:
a first generator for generating a submillimeter wave frequency optical radiation signal beam;
a second generator for generating a submillimeter wave frequency optical radiation reference beam having a frequency that is different from the signal beam;
a first beam splitter for dividing the signal beam into first and second portions;
means for scanning the first portion of the signal beam with respect to the sample;
a second beam splitter for dividing the reference beam into first and second portions;
a first mixer for mixing the first portion of the signal beam after interaction with the sample with the first potion of the reference beam to create a measurement intermediate frequency signal;
a second mixer for mixing the second portion of the signal beam and the second portion of the reference beam to create a reference intermediate frequency signal; and
a processor for processing the measurement and reference intermediate frequency signals in order to derive magnitude and phase information as a function of position of the first portion of the signal beam on the sample, said magnitude and phase information capable of being converted into image information.

31. A system as recited in claim 30, wherein the processor functions to determine the relative phase difference between the measurement and reference intermediate frequency signals.

32. A system as recited in claim 30, wherein the processor includes a lock-in amplifier.

33. A system as recited in claim 30, wherein said scanning means laterally scans the first portion of the signal beam with respect to the sample to generate two-dimensional image information.

34. A system as recited in claim 33, further including a display for displaying the two dimensional image information.

35. A system as recited in claim 34, wherein the displayed image information is relative power as a function of scan position.

36. A system as recited in claim 30, wherein the signal beam interacts with the sample through transmission.

37. A system as recited in claim 30, wherein said signal beam interacts with the sample by reflection.

* * * * *